United States Patent [19]

Watanabe et al.

[11] Patent Number: 4,678,566
[45] Date of Patent: Jul. 7, 1987

[54] APPARATUS FOR SEPARATING PROTEINS FROM BLOOD PLASMA

[75] Inventors: Masaharu Watanabe, Tama; Hiroaki Ohe, Fuji, both of Japan

[73] Assignee: Terumo Kabushiki Kaisha, Tokyo, Japan

[21] Appl. No.: 753,713

[22] Filed: Jul. 10, 1985

[30] Foreign Application Priority Data

Jul. 20, 1984 [JP]  Japan ............................ 59-149311
Sep. 7, 1984 [JP]  Japan ............................ 59-187805

[51] Int. Cl.⁴ ..................... B01D 21/00; C07K 3/21
[52] U.S. Cl. ........................... 210/143; 210/201; 210/206; 210/321.3; 210/416.1; 210/418; 210/905; 210/927; 530/418; 530/419
[58] Field of Search ............... 260/112 B; 530/364, 530/380, 418, 419; 604/4, 5, 6; 210/143, 201, 205, 206, 321.3, 416.1, 418, 434, 905, 927

[56] References Cited

U.S. PATENT DOCUMENTS

| | | | |
|---|---|---|---|
| 4,321,192 | 3/1982 | Jain | 604/6 X |
| 4,322,275 | 3/1982 | Jain | 210/927 X |
| 4,381,775 | 5/1983 | Nosé et al. | 604/6 |
| 4,401,430 | 8/1983 | Dorson, Jr. et al. | 604/4 |
| 4,582,598 | 4/1986 | Bilstad et al. | 210/927 X |

FOREIGN PATENT DOCUMENTS 0074610  3/1983  European Pat. Off. .

Primary Examiner—Richard V. Fisher
Assistant Examiner—W. Gary Jones
Attorney, Agent, or Firm—Frishauf, Holtz, Goodman & Woodward

[57] ABSTRACT

An apparatus is provided for reacting a solution of a precipitating medium of alkaline metal chlorides at a fixed rate of delivery with plasma continuously separated from blood, filtering the precipitate formed by the reaction, removing the solution of precipitating medium from the plasma following the use of the medium, adjusting the purified treated plasma, and returning the purified plasma to the blood in an amount equivalent to that of the continuously separated plasma. To enhance the precipitative separating action of alkaline metal chloride on plasma protein without detracting from the advantages of the alkaline metal chloride, use is made of a solution of precipitating medium comprising a mixture of the alkaline metal chloride and an amino acid, the latter being added in an amount sufficient to promote the precipitating effect of the alkaline metal chloride.

6 Claims, 6 Drawing Figures

APPARATUS FOR SEPARATING PROTEINS FROM BLOOD PLASMA

BACKGROUND OF THE INVENTION

1. Field of the Invention

This invention relates to an agent for the separation and removal of proteins from blood plasma by the salting-out effect, and to an apparatus which utilizes the agent to separate and remove specific proteins such as immune complexes, immunoglobulins, fibrinogen and other soluble macromolecular proteins from blood plasma. The apparatus is used in removing pathogenic substances from a large quantity of collected blood followed by reinfusion of the blood, and in the purification of plasma by removal of pathogenic substances from a large quantity of pool blood.

2. Description of the Prior Art

It is becoming clear that immunoglobulins, immune complexes, complement, fibrinogen and other soluble macromolecular substances contained in blood play a role in causing autoimmune diseases, rheumatoid arthritis and other antigenic diseases. These disease treated by a plasma exchange process which includes removing plasma containing the harmful substances from the patient's blood and replacing the plasma with a substitute fluid. This process was first used in 1963 for the treatment of macroglobulinemia and since then has been tried in the treatment of many illnesses. With the development in recent years of membrane-type plasma separators, plasma exchange has become simpler and, hence, more widely practiced. However, the wider application of this treatment has been accompanied by increased consumption of the substitute fluids (e.g., FFP, agents made of albumin and the like) the supply of which has, as a result, become limited and higher in cost. An additional problem is that the infusion of a large quantity of human plasma ca bring about unwelcome side effects such as hepatitis, alergic reactions and serum sickness.

A method now undergoing research for dealing with the foregoing problems is so-called plasma purification or cleansing which, rather than relying upon a substitute fluid, selectively removes the macromolecular proteins causing the particular illness from the patient's blood plasma and reinfuses the patient with his or her own cleansed blood plasma containing albumin and other useful plasma ingredients. Plasma purification processes known so far include a process for removing macromolecular protein from blood plasma by using a membrane having a pore diameter smaller than that of a plasma separating membrane, and a process for the adsoptive removal of macromolecular protein from blood plasma by relying upon an adsorbent. While the former has tentatively shown some efficacy in clinical use and has won some standing as a curative means, the latter is still in the basic research stage and only partial clinical use has been reported. Both processes have drawbacks in that the former exhibits insufficient selectivity in terms of removing specific proteins and the latter is incapable of treating a large quantity of plasma at one time. Thus, neither process is truly adequate. Accordingly, there is a need to develop a more effective and efficient apparatus for purifying blood plasma.

In view of these circumstances, the applicant has filed patent applications for inventions the gist of which is to use a chloride of an alkaline metal, e.g., sodium chloride, as an agent, or precipitating medium, for separating proteins from plasma by the salting-out effect. The applications filed are Japanese patent application Nos. 58-207463 and 58-207464. The proposed separating agent, owing to its weak salting-out action and low solubility in blood plasma, is effective in causing the specific precipitation solely of macromolecular proteins such as fibrinogen and immuno-globulins without resulting in the precipitation of such useful proteins of low molecular weight as albumin, even if the rate at which the agent is added to plasma is greater than that required for saturation.

SUMMARY OF THE INVENTION

An object of the present invention is to solve or mitigate the aforementioned problems involved in supplying a substitute fluid in plasma exchange treatment, and to facilitate the implementation of the plasma exchange treatment, by providing an apparatus for the separation and removal of proteins from blood plasma, which apparatus is improved in terms of structure and function to fractionate various proteins from blood plasma selectively and in large quantities by utilizing a difference in solubility.

Another object of the present invention is to provide an agent for the precipitative separation of proteins from blood plasma, which agent retains the advantages of the abovementioned alkaline metal chloride while exhibiting an improved separating action against plasma proteins.

Still another object of the present invention is to provide an apparatus which uses the aforementioned plasma protein separating agent to separate and remove proteins from blood plasma.

According to the present invention, the first-mentioned object is attained by providing an apparatus for the separation and removal of proteins from blood plasma, which apparatus includes a plasma pump for delivering plasma from a living body and for returning treated plasma to the living body in an amount equivalent to that of the plasma delivered, a vessel for accommodating a solution of a precipitating medium for causing precipitation of a predetermined protein constituent in the plasma, a precipitating medium solution pump operatively associated with the plasma pump for delivering the solution of precipitating medium at a fixed delivery rate, a mixer for mixing the delivered plasma and the delivered solution of precipitating medium, whereby a precipitate is formed in the mixer, a plasma filter for removing the precipitate formed in the mixer, thereby resulting in filtered plasma, a plasma constituent adjusting unit for removing the precipitating medium from the filtered plasma and for producing the abovementioned treated plasma by adjusting water content and electrolyte, and a control unit for driving and controlling the plasma pump and the precipitating medium solution pump.

According to an embodiment of the present invention, the plasma constituent adjusting unit comprises a further plasma pump operatively associated with the plasma pump for operating at a flow rate equal to or less than the delivery flow rate of the plasma pump, plasma concentrating means operatively associated with the further plasma pump for removing water from the plasma in an amount equal to or more than that of the added solution of precipitating medium, thereby resulting in concentrated plasma, and precipitating medium removing means for removing the precipitating medium from the concentrated plasma and for adjusting the electrolyte of the concentrated plasma.

According to embodiments of the present invention, the precipitating medium solution is a solution of various inorganic salts, a solution of various organic solvents, or a solution of an inorganic or organic acid.

It should be noted that the plasma proteins mentioned herein refer to proteins present in the liquid fraction that results when tangible constituents, namely blood cells (red blood cells, white blood cells and platelets) are removed from blood. Though these plasma proteins may be broadly classified into albumin, globulins ($\alpha_1$, $\alpha_2$, $\beta$, $\gamma$) and fibrinogen, a further subdivision into some 80 types now known can be made by a more detailed analysis, these proteins including transferrin, haptoglobin, hemopexin, glocoprotein, riboprotein, immunoprotein, compliment and immune complex enzyme. Furthermore, plasma proteins can also be broadly classified into proteins of high and low molecular weight. The former, namely macromolecular protein, refers to immunoglobulins, immune complexes, compliment, fibrinogen and the like, while the latter refers to albumin, etc.

The plasma protein separating agent and apparatus of the present invention are used for the extraction mainly of macromolecular proteins.

According to the present invention, the second-mentioned object is attained by providing an agent for the precipitative separation of proteins from blood plasma comprising, as an active ingredient, a mixture of an alkaline metal salt and an amino acid in an amount sufficient to promote the fractional precipitating effect of the alkaline metal salt with respect to plasma protein, the amino acid being at least one selected from the group consisting of neutral amino acid, aspartic acid, cystine, N-acetyltryptophan and tyrosine.

Further, according to the present invention, the third-mentioned object is attained by providing an apparatus for the separation and removal of proteins from blood plasma including a vessel for accommodating an agent for the precipitative separation of proteins from blood plasma, the agent comprising, as an active ingredient, a mixture of an alkaline metal salt and an amino acid in an amount sufficient to promote the fractional precipitating effect of the alkaline metal salt with respect to plasma protein, the amino acid being at least one selected from the group consisting of neutral amino acid, aspartic acid, cystine, N-acetyltryptophan and tyrosine, means for introducing plasma into the vessel, means for separating and removing a precipitate formed inside the vessel by bringing the separating agent and the plasma into contact, and means for removing at least some of the separating agent constituent from the plasma component which remains following removal of the precipitate.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Blood plasma contains proteins of a high molecular weight, such as immune complexes, immunoglobulins and fibrinogen, as well as proteins of a comparatively low molecular weight, such as albumin. There is a need in self-purifying plasma treatment to selectively remove only the proteins of high molecular weight and leave the plasma with the useful proteins of low molecular weight, such as albumin. The inventors have conducted extensive research with regard to media capable of precipitating proteins in plasma and as a result have found that alkaline metal chlorides, particularly sodium chloride, owing to their comparatively weak salting-out action and low solubility, cause specific precipitation solely of the macromolecular proteins such as fibrinogen and immunoglobulins with hardly any precipitation of albumin, even if the medium, say sodium chloride, is added to the plasma in an amount greater than that required for saturation. More specifically, the inventors have discovered that if the sodium chloride added for separating and removing the precipitate formed by mixing the precipitating medium with plasma is maintained in the plasma at an amount above that needed for saturation, then strict control is unnecessary, and that there is no change in the effectiveness of precipitation or in the composition of the precipitate, as well as no change in the properties of the protein, even at the high level of sodium chloride addition. Based on the fruits of this research, the inventors have perfected the present apparatus which is capable of purifying blood by separating solely the macromolecular proteins from a large quantity of blood plasma by on-line implementation of the steps of plasma separation, precipitate formation, removal of the precipitate and recovery of the processed plasma.

Preferred embodiments of the present invention will now be described with reference to the accompanying drawings.

Figure 1:
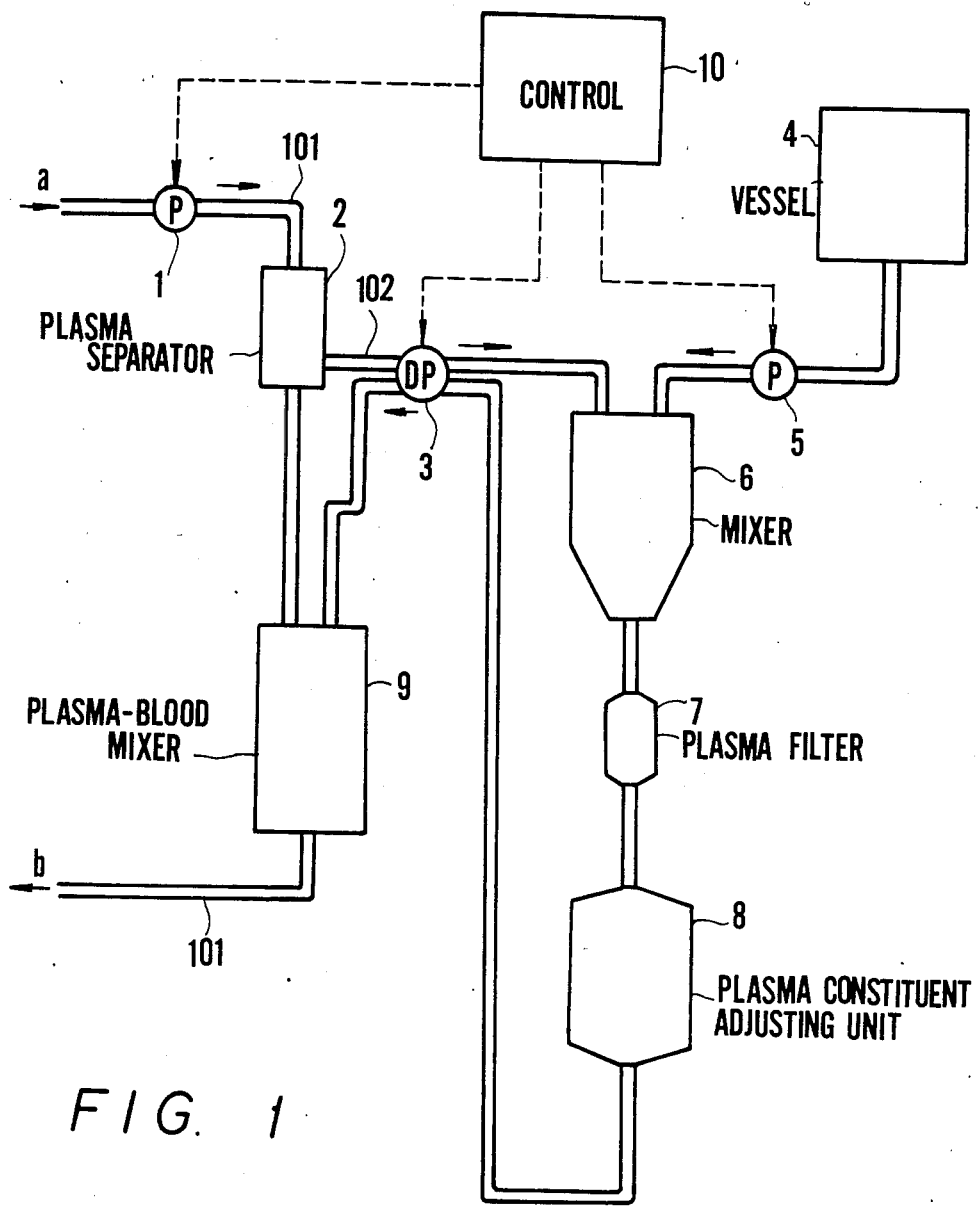
FIG. 1 is a block diagram illustrating a preferred embodiment of a blood purifying apparatus according to the present invention.

FIG. 1 is a block diagram illustrating a blood purifying system according to an embodiment of the inventive apparatus for the separation and removal of a protein constituent from blood plasma. A blood pump 1 delivers blood collected from a patient into a main conduit 101 made of, e.g., vinyl chloride. The main conduit 101 is connected to a plasma separator 2 which, by centrifugal- or membrane-type separation, separates the blood entering from the conduit into plasma and blood cell fractions. The separated plasma from the separator 2 is fed into a secondary conduit 102, also made of vinyl chloride, by a double roller-type plasma pump 3 which, at the same time, returns processed blood plasma in amount equivalent to the plasma drawn from the patient. A vessel 4 containing a solution of a precipitating medium is connected to a precipitating medium solution pump 5 operatively associated with the plasma pump 3 for delivering the solution of precipitating medium from the vessel 4 at a fixed feed ratio. A mixer 6 receives plasma delivered by the plasma pump 3 and the solution of precipitating medium delivered by the pump 5 for mixing the two together. The outlet of the mixer 6 is connected to a plasma filtering unit 7 for removing a protein fraction which has precipitated inside the mixer 6. The outlet of the plasma filtering unit 7 is in turn connected to a plasma constituent adjusting unit 8 for removing the precipitating medium from the filtered plasma and for adjusting water content and electrolyte. The processed plasma following its adjustment in the adjusting unit 8 is fed by the pump 3 into a plasma mixing unit 9, where the plasma is mixed and rejoined with the concentrated blood comprising the blood cells originally separated from the incoming blood by the plasma separator 2. A control unit 10 acts through the blood pump 1, plasma pump 3 and precipitating medium solution pump 5 to control the amounts of blood, plasma and precipitating medium solution delivered.

With the above-described arrangement, the patient's blood introduced from a blood inlet a is cleansed automatically and continuously before being returned to the patient from a blood outlet b. More specifically, blood drawn from the patient is introduced by the blood pump 1 into the plasma separator 1, where the blood is separated into blood cell and plasma fractions. The plasma resulting from the separation is led into the secondary conduit 102 by the plasma pump 3 and flows into the mixing unit 6. Meanwhile, the solution of precipitating medium in the vessel 4 is delivered to the mixing unit 6, in which mixing with the plasma takes place, by the plasma medium solution pump 5 rotated at a fixed ratio in operative association with the plasma pump 3. A precipitate (mainly fibrinogen and globulin fractions) that forms in the mixing unit 6 is filtered out by the plasma filtering unit 7 for precipitate removal. The resulting filtered plasma, which still contains the precipitating medium, flows from the filtering unit 7 into the plasma constituent adjusting unit 8. Here the processed plasma is submitted to dewatering, removal of the precipitating medium and adjustment of electrolyte before being delivered to the plasma mixing unit 9 by the double roller-type plasma pump 3 in an amount equivalent to that of the plasma collected from the patient. The processed plasma mixes with the concentrated blood delivered by the plasma separator 2 and the mixture of processed plasma and concentrated blood is reinfused into the patient from the blood outlet b.

Examples of the solution of the precipitating medium for protein separation are solutions of a variety of salts, namely alkaline metal salts such as sodium chloride, potassium chloride, sodium sulfate, potassium phosphate and sodium citrate, ammonium salts such as ammonium sulfate, and the like. In particular, when an alkaline metal salt is used, the amount of salt added need not be strictly controlled, for it will suffice if control is exercised such that the amount of salt added is maintained above that necessary for causing the macromolecular proteins to precipitate out of the plasma. In addition, though it is possible to use an organic solvent such as ethanol, an inorganic acid such as hydrochloric acid or sulfuric acid or an organic acid such as ascorbic acid, there is the possibility of a change in properties of the proteins when these substances are employed. It is therefore necessary to provide a set-up in which close attention is paid to temperature measurement and control of pH at mixing.

The control unit 10 sets and regulates the rotating ratios of the pumps 3 and 5 mainly in dependence upon both the concentration of the precipitating medium solution and the protein that is desired to be removed from the plasma and is adapted to control the average flow rates of these motors so as to mix in an amount of the precipitating medium solution prescribed in accordance with the amount of plasma. For example, if ammonium sulfate is used as the precipitating medium solution, fibrinogen will substantially precipitate at an ammonium sulfate concentration in plasma of about 10 g/dl, and both fibrinogen and gamma-globulin will substantially precipitate at an ammonium concentration in plasma of about 20 g/dl. Therefore, in case of a saturated solution (about 54 g/dl), each of the proteins can be made to precipitate and separate from the plasma if the settings are such as to add the ammonium sulfate at rates of about 23 ml and 59 ml, respectively, with respect to 100 ml of plasma. It takes about 10 to 20 mS for this chemical reaction. Flow rate control of this kind can readily be executed under the control of a microprocessor equipped with the control program of FIG. 3, described later.

A dialyzer used in ordinary dialysis is adopted as the plasma constituent adjusting unit 8. Any dialyzer configuration will suffice providing that it has a dewatering capability that enables removal of the added amount of precipitating medium solution at less than the usable pressures, as well as a dialyzing capability that enables the concentration of the precipitating medium to be brought below a stipulated value.

Figure 2:
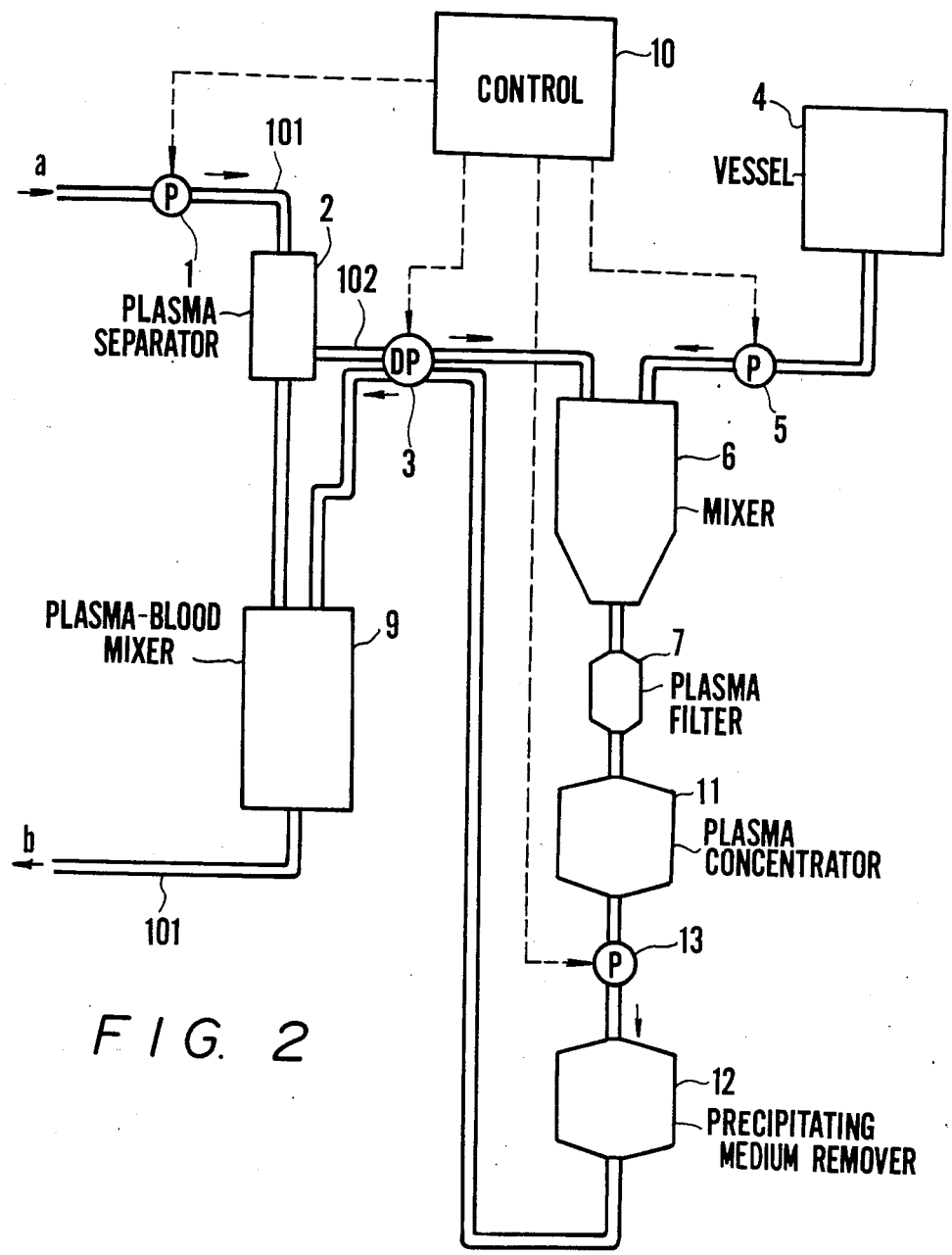
FIG. 2 is a block diagram illustrating another preferred embodiment of a blood purifying apparatus according to the present invention.

FIG. 2 is a block diagram showing a blood purifying system according to another embodiment of the present invention. Portions similar to those shown in FIG. 1 are designated by like reference characters and need not be described again. In this arrangement, the dewatering and dialysis processes performed by the plasma constituent adjusting unit 8 of FIG. 1 are performed separately at different stages. Specifically, the plasma filtered by the filtering unit 7 for precipitate removal is fed into a plasma concentrating unit 11 where the plasma is dewatered to a degree no less than the amount of precipitating medium solution added. The dewatering process is performed by a plasma pump 13 operatively associated with the plasma pump 3 and controlled to provide a flow rate equal to or less than that of the plasma pump 3. Next, the concentrated plasma from the concentrating unit 11 is fed into a precipitating medium removal unit 12, where residual precipitating medium is removed and electrolyte adjusted. The resulting plasma is then delivered to the plasma mixing unit 9 by the double roller-type pump 3 in an amount equivalent to that of the plasma collected. The concentrated blood delivered by the plasma separator 2 mixes with the plasma in mixing unit 9, whence the resulting mixture is reinfused into the patient from the blood outlet b.

Figure 3:
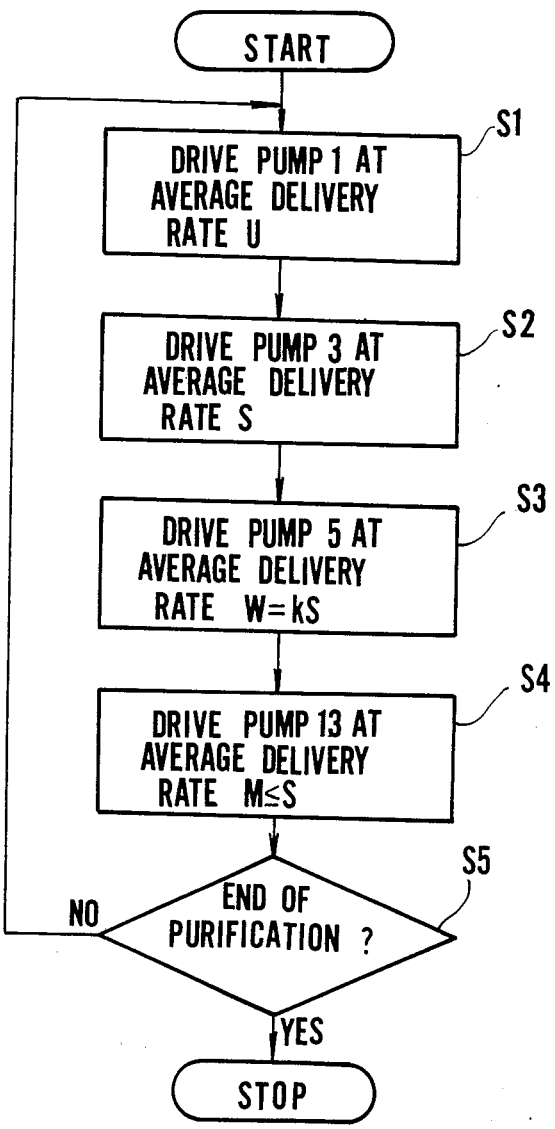
FIG. 3 is a flowchart illustrating flow rate control performed by a control unit in the apparatus of FIG. 2.

FIG. 3 is a flowchart illustrating an embodiment of flow rate control executed by the control unit 10 of FIG. 2. Flow rate control is the same for FIG. 1 with the exception of the control step involving the plasma pump 13, which is not provided in the apparatus of FIG. 1. The first step S1 of the flowchart calls for the pump 1 to be driven and controlled at an average delivery rate U (e.g., 60 to 100 ml/min) set as the average flow rate at which blood is to be collected from a patient. The next step S2 calls for the double roller-type pump 3 to be driven and controlled at an average delivery rate S (e.g., 15 to 40 ml/min) determined in relation to the delivery rate U. Next, at a step S3, a rate k at which the solution of precipitating medium is to be delivered is determined in dependence upon the kind of plasma protein to be precipitated, and the pump 5 is driven and controlled at an average delivery rate W (=k S) determined based on k. This is followed by a step S4, at which dewatering is performed to a degree no less than the amount of precipitating medium solution added. To this end, the pump 13 is driven and controlled in operative association with the plasma pump 3 and at an average delivery rate M ($\leq$ S), namely at a rate equal to or less than at which the plasma pump 3 is driven. It is then decided at a step S5 whether purification has ended. If the decision here is affirmative, all pumps are stopped; if negative, the control sequence is continued from step S1. In order to avoid too much hemolysis, transmembrane pressure (TMP) is controlled so as not to exceed 45 mmHg.

Thus, the invention provides an apparatus capable of highly efficient separation and removal of macromolecular proteins such as immunoglobulins and fibrinogen contained in blood plasma. Preferably, an alkaline metal chloride such as sodium chloride or potassium chloride is used as the protein precipitating medium. A precipitating medium of this type will neither alter the effectiveness of precipitation nor change the properties of the protein in the plasma even if the medium is added to the plasma in large quantities. This provides a high level of stability even when large quantities of plasma are submitted to the purification treatment. In addition, since the precipitating medium selectively precipitates solely the proteins of large molecular weight such as immunoglobulins and fibrinogen but causes almost no precipitation of the useful proteins of low molecular weight such as albumin, the useful constituents (albumin, etc.) can be reinfused into the patient following the self-purification of the patient's blood; hence, a substitute fluid used in plasma exchange treatment is unnecessary. This solves the problems encountered in the prior art, namely the side effects such as hepatitis and allergic reactions, the high cost and the scarcity of substitute fluid supplies. Further, according to the present invention, the process for separating and removing protein consituents from blood plasma can be practiced on-line, thereby shortening overall processing time and reducing the danger of bacterial infection.

The inventors have conducted extensive research with regard to alkaline metal chorides such as sodium chloride in an effort to improve the precipitative separating action thereof with respect to plasma proteins. As the result of this research, the inventors have found that the precipitative separating action of these chlorides can be greatly improved, without detracting from the earlier mentioned advantages thereof, by blending with an alkaline metal chloride at least one amino acid selected from the group consisting of neutral amino acid, aspartic acid, cystine, N-acetyltryptophan and tyrosine. The inventors have also found that these amino acids enhance the plasma protein-separating action not only of alkaline metal chlorides but also of other salts of alkaline metals.

The alkaline metal salt constituting the effective ingredient of the plasma protein-precipitative separating agent of the present invention includes chlorides such as sodium chloride, potassium chloride, lithium chloride, rubidium chloride, cesium chloride and francium chloride, and further includes sulfates such as sodium sulfate. Among these alkaline metal salts, the effect of adding the amino acid is best exhibited for the chlorides, as will be set forth below. It has been mentioned earlier that alkaline metal chlorides have the effect of selectively precipitating only harmful macromolecular proteins, especially immunoglobulins, without precipitating useful plasma constituents such as albumin even when the chlorides are added in an amount in excess of that needed for saturation. This is of great convenience in terms of controlling the concentration of the separating agent with respect to plasma. Sodium sulfate, on the other hand, exhibits a strong salting-out effect and can result in the precipitation of the useful plasma constituents such as albumin if mixed with plasma at too high a percentage. This therefore necessitates strict control of the added sodium sulfate concentration. However, the salting-out effect even of sodium sulfate can be enhanced by blending it with an amino acid in accordance with the present invention.

It has been set forth earlier in the specification that harmful proteins are precipitated out of blood plasma, the precipitate is removed, the plasma protein-separating agent used is subsequently removed from the purified plasma fraction, and the resulting plasma is returned to the patient. Therefore, it is preferred that the alkaline metal salt used be readily removable from the purified plasma fraction and safe as far as the patient is concerned. Seen in this light, the most desirable alkaline metal salts that can be used are chlorides, especially sodium chloride and potassium chloride, which exist naturally in the human body.

According to the invention, the amino acids blended with the abovementioned alkaline metal salts are neutral amino acids (e.g., glycine, alanine, valine, leucine, isoleucine), aspartic acid, tyrosine, N-acetyltryptophan and cystine. A mixture of any two or more of these may also be used. The neutral amino acids are the most effective among these amino acids, with glycine being the most useful.

Enhancement of the plasma protein-separating effect of the alkaline metal salt is brought about by the addition thereto of the abovementioned amino acid at a proportion of 5 to 50 wt-% with respect to the total weight of the alkaline metal chloride - amino acid mixture. It is preferred that the amino acid be blended with the alkaline metal salt at a proportion of 10 to 45% with respect to the total weight of the alkaline metal chloride - amino acid mixture.

As to the ratio of added separating agent to plasma, the amount of separating agent added should be enough for the alkaline metal salt to manifest its plasma separating effect, namely its selective precipitating effect. More specifically, the amount of separating agent added is more than that needed to raise the alkaline metal salt concentration in plasma to saturation.

It is generally considered that salting out occurs due to neutralization of the electric charges of the colloid in the aqueous solution. The alkaline metal salt added to the plasma prote in dissociates into ions in the plasma and selectively neutralizes and precipitates the harmful macromolecular proteins, especially the globulins. Though the mechanism through which the addition of amino acid enhances the salting-out effect is not yet known in terms of theory, it seems that the amino acid acts in some way upon the plasma protein constituent to thereby raise the effectiveness at which salting-out takes place.

Figure 4:
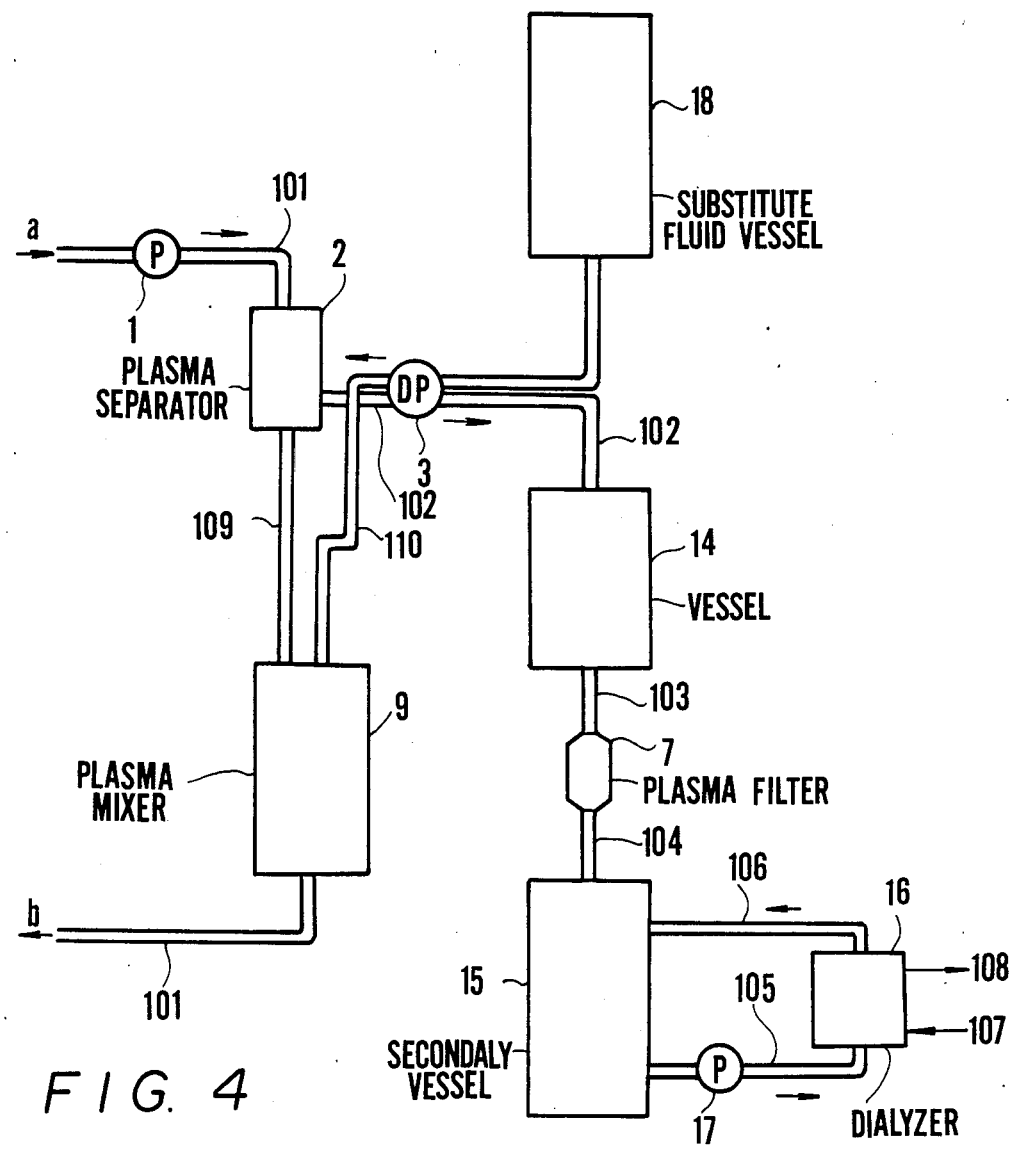
FIG. 4 is a block diagram illustrating still another preferred embodiment of a blood purifying apparatus adapted for batch processing according to the present invention.

FIG. 4 is a block diagram illustrating another embodiment of a blood purifying system for selectively precipitating and removing, by so-called batch processing, macromolecular proteins from blood plasma through use of the plasma protein-separating agent of the present invention. Portions similar to those shown in FIGS. 1 and 2 are designated by like reference characters and are not described again in detail.

Blood drawn from a patient is fed into the plasma separator 2 through the main conduit 101 by the plasma pump 1. The plasma separator 2 separates the incoming blood into a blood cell fraction and plasma fraction, with the latter being fed into the secondary conduit 102 by the plasma pump 3 and thence to a vessel 14, which accommodates the plasma protein-separating agent, namely the precipitating medium, of the present invention.

The plasma fraction introduced into the vessel 14 mixes with the separating agent of the present invention so that the macromolecular proteins in the plasma are precipitated. After being left standing for from 1 to 200 hours, the contents of the vessel 14 are fed into a precipitate separator, e.g., the plasma filter 7, through a conduit 103. The filter 7 separates and removes the precipitate from the plasma, producing a cleansed plasma fraction with is received in a secondary vessel 15 via a conduit 104. Connected to the secondary vessel 15 via conduits 105, 106 is means, e.g., a hollow fiber-type dialyzer 16, for removing the plasma-protein separating agent from the plasma. The cleansed plasma fraction in the secondary vessel 15 is fed into the dialyzer 16 via the conduit 105 by the pump 17 and then flows back into the secondary vessel 15 via the conduit 106. This circulation of the cleansed plasma fraction is repeated as often as desired. The cleansed plasma fraction in the dialyzer 16 is dialyzed for removal of the plasma-protein separating agent by a dialyzing solution, such as any readily available for use in ordinary artificial dialysis, which is passed through the interior of the dialyzer 16 via conduits 107, 108. If sodium chloride and (or) potassium chloride, which are constituents of body fluids, are used as the alkaline metal component in this case, complete removal thereof by dialysis is unnecessary, for it will suffice if the chlorides are removed to provide a concentration thereof equivalent to that found in the blood of the human body. The secondary vessel 15 containing the plasma fraction thus cleansed and purified is exchanged with a substitute fluid vessel 18, described below, and is reinfused into the patient through a path identical with that used for infusing a substitute fluid.

The blood cell fraction separated by the plasma separator 2 is returned to the patient through a conduit 109. Prior to that, however, the blood cell fraction is mixed in the mixing unit 9 with a substitute fluid (also referred to in the art as a replacement or make-up fluid), such as physiological saline or a 5% albumin solution, which is contained in the vessel 18 and introduced into the mixer 9 through a conduit 110 by the pump 3. The reason for introducing the substitute fluid is that purified and cleansed plasma, obtained in the manner described above, is not yet ready at the initial stage of the plasma purifying operation. When cleansed and purified plasma is prepared in the above-described fashion, the substitute fluid vessel 18 is replaced by the secondary vessel 15 containing the purified plasma and the purified plasma is returned to the patient through the same path used for infusing the abovementioned substitute fluid.

Figure 5:
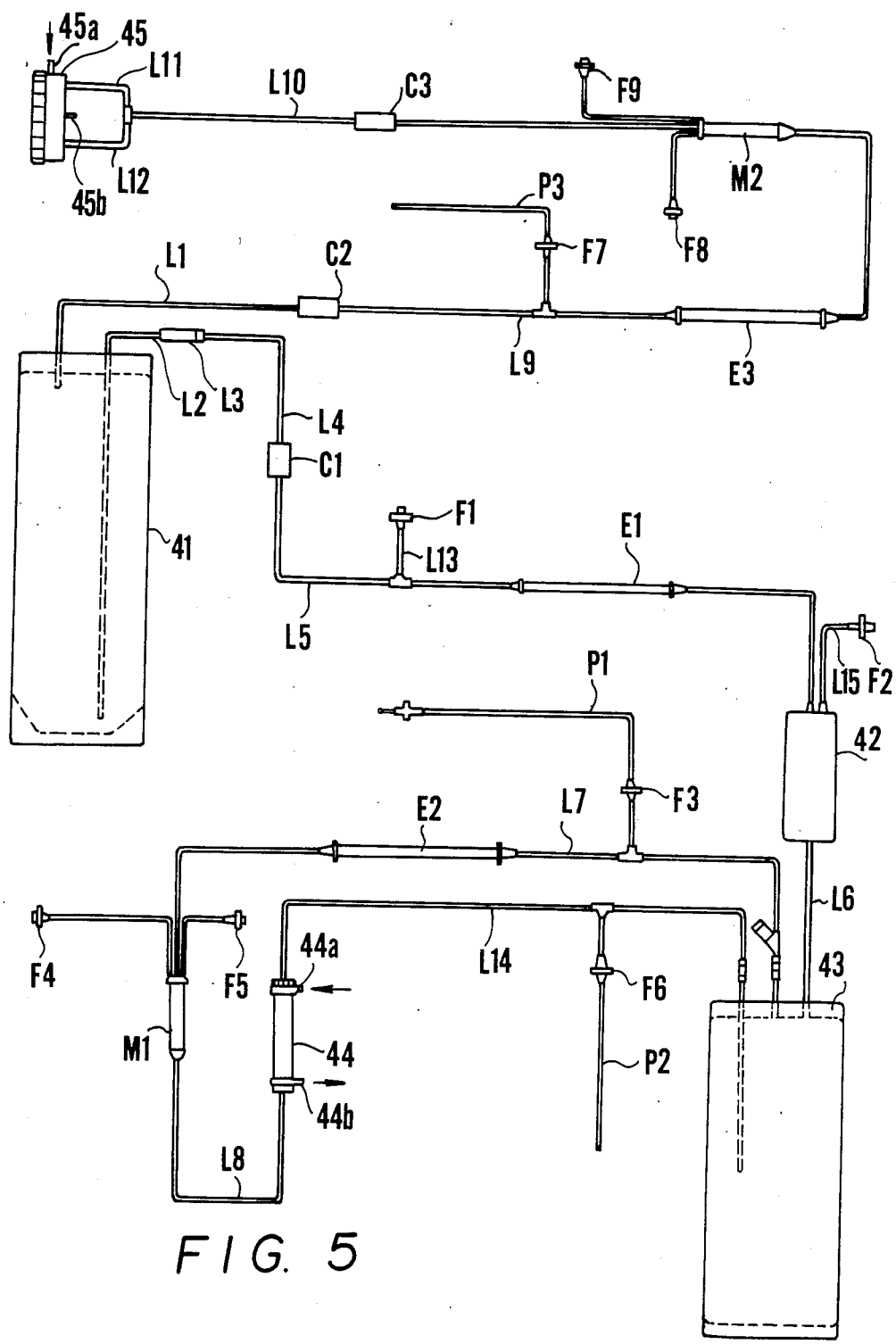
FIG. 5 is a plan view illustrating the blood purifying apparatus of FIG. 4 in greater detail.

FIG. 5 shows in greater detail the plasma protein-separating apparatus described above with reference to FIG. 4. The apparatus includes a flexible bag 41 serving as vessel for receiving blood plasma. The bag 41 comes equipped with a supply of the separating agent of the present invention and has a tube L1 serving as a plasma inflow passage and a tube L2 serving as a plasma outflow passage. The tip of the tube L1 situated inside the bag 41 is closed. Provided in the wall of the tube L1 at a location distanced slightly from the tip thereof is a notch (not shown). By tearing away the tip of the tube L1 at the notched portion thereof at use, the interior of the tube can be brought into communication with the interior of the bag 41. The end of the tube L2 outside the bag 41 is closed. Formed in the wall of the tube L2 at a location distanced slightly from the tip at said end thereof is a notch similar to that described above. The tube L2 is connected to a tube L4 communicating with a precipitate removal filter 42, described below, by a tube L3 of a larger diameter. The tube L3 is so arranged that the notched portion of the tube L2 is situated therein. At use, the tubes L2, L4 are communicated by tearing away the notched portion of the tube L2.

The tube L3 is connected with the filter 42 via tubes L4, L5 in the above-described manner. The tubes L4, L5 are aseptically interconnected by a connector C1, described below. The precipitate removal filter 42 is for the purpose of filtering out a precipitate formed in the bag 41 by contact between the plasma fraction and the plasma protein-separating agent of the present invention. The filtered liquid, namely the cleansed plasma, from the filter 42 is collected in a secondary bag 43 via tube L6.

A tube L14 has one end inserted deeply in the interior of the secondary bag 43. The other end of tube L14 is connected to one end of a hollow fiber-type dialyzer 44. Connected to the other end of the dialyzer 44 is one end of a tube L8, the other end whereof is connected to the secondary bag 43. The tubes L14 and L8 form a closed circuit. The filtered liquid in the secondary bag 43 is circulated through this closed circuit in order to be dialyzed to the degree desired. The dialyzing solution is introduced into the dialyzer 44 from an inlet 44a and flows out of the dialyzer from an outlet 44b.

The end of the tube L1 outside the bag 41 is connected to a tube L9 via a connector C2, described below. The tube L9 is in turn connected to a tube L10 via a connector C3, described below. Plasma outflow tubes L11, L12 of a plasma separating filter 45 merge and are connected to a tube L10. Blood introduced into the plasma filter 45 from a blood inlet 45a thereof is separated by the filter 45 into a plasma fraction and blood cell fraction. The blood cell fraction exits from a discharge portion 45b of the filter 45.

Connected to the tube L5 is a tube L13 for venting internal air or for introducing ambient air. Connected to one end of the tube L13 is an antibacterial filter F1 which allows the passage of air therethrough but which is impermeable to liquid. The filter F1 prevents the intrusion of bacteria present in the outside air. Arranged in the tube L5 is a flexible tube E1 driven by a pump to induce the outflow of the contents in bag 41. An antibacterial filter F2, similar to the filter F1, is connected to the precipitate-removing filter 42 via a tube L15.

Connected to a tube L7 is a priming tube P1 having a filter F3 arranged in a section thereof. A flexible tube E2 similar to the flexible tube E1 is arranged upstream of the tube L7. A pressure monitor M1 is arranged in a tube L8 to monitor pressure internally of the tube. A priming tube P2 having a filter F6 disposed in a section thereof is connected to the tube L14. Antibacterial filters F4, F5, similar to those mentioned above, are connected to the pressure monitor M1. Likewise, a priming tube P3 having a filter F7 arranged in a section thereof is connected to the tube L9. Arranged upstream of the tube L9 are a flexible tube E3 and a pressure monitor M2.

The connector C1 interconnecting the tubes L4, L5, the connector C2 interconnecting the tubes L1, L9, and the connector C3 interconnecting the tubes L9, L10 are all adapted to make these connections in an aseptic manner. A connector of such type is as disclosed in the specification of Japanese patent application Laid-Open No,. 57-211353. The disclosed connector comprises first and second connector portions. The first connector portion, in the shape of a short tube of a requisite length, is made of a heat- and corrosion-resistant material (such as a ceramic, stainless steel, titanium) and has a male engagement portion including a plug side formed in a male mold. The second connector portion, also in the shape of a short tube of a requisite length, is made of a heat- and corrosion-resistant material and has a female engagement portion including a plug end formed in a female mold, the female engagement portion mating with the male engagement portion of the first connector portion. The two connector portions are locked together by a locking mechanism which does not rely upon threaded engagement, and the sides of the connectors that are connected to the respective tubes are each covered by a fitted cylindrical supporting body made of an adiabatic material (such as silicone rubber, Teflon resin or cork). With a connector of this type, the first and second connector portions are capable of being connected together while being directly heated by application of a flame, thereby assuring sterilization. This makes it possible to achieve an aseptic connection.

Among the connectors of this type disclosed in the abovementioned specification of the laid-open application, those illustrated in FIGS. 5 and 11 of the specification, and above all in FIG. 11, are particularly well-suited for use as the connectors C1, C2, C3 of the protein separating apparatus of the present invention. One example of these connectors will now be described with reference to FIG. 6.

Figure 6:
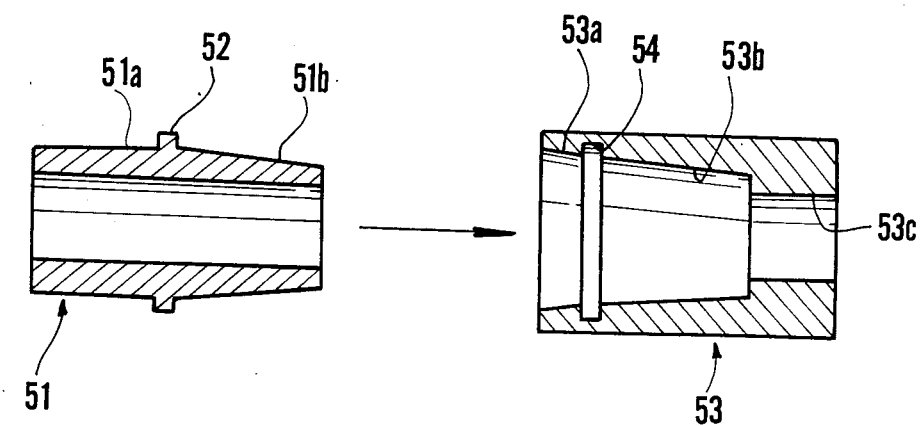
FIG. 6 is a sectional view of a connector for aseptically connecting tubes in the blood purifying apparatus of FIG. 5.

The connector depicted in FIG. 6 comprises a first cylindrical body 51 made of a heat- and corrosion resistant material and corresponding to the abovementioned first connector portion, and a second cylindrical body 53 made of a heat- and corrosion resistant material and corresponding to the abovementioned second connector portion. The first cylindrical body 51 has an inner diameter which is the same over the entire length thereof, and a surface formed by a flat portion 51a which is parallel to the inner surface of the body, and a tapered portion 51b which tapers from the flat portion 51a to the end of the body. An annular projection 52 is formed at the boundary of the flat portion 51a and tapered portion 51b. The second cylindrical body 53 has an outer diameter which is the same over its entire length and comprises an end portion 53a having an inner diameter which grows successively larger as the outer side of the end portion is approached and which is greater than the outer diameter of the flat portion 51a of cylindrical body 51, a tapered portion 53b having an inner surface corresponding to the surface of the taper portion 51b of cylindrical body 51, and a flat portion 53c having an inner diameter equal to that of the cylindrical body 51. Formed in the inner surface of the cyllindrical body 53 is an annular groove 54 corresponding to the annular projection 52 of the cylindrical body 51. When the cylindrical body 51 is pressed into cylindrical body 53 in the direction of the arrow, the cylindrical body 53 spreads slightly at its end portion 53a to receive the cylindrical body 51, the annular projection 52 whereof mates with the annular groove 54 of the cylindrical body 53 to lock the bodies 51, 53 together.

EXAMPLE 1

Human plasma was mixed with sodium chloride and glycine and was left standing for 16 hr, followed by filtering the precipitate that formed. The amount of sodium chloride used was 30 g/dl plasma, and the amount of glycine added (g/dl) was varied with respect to the amount of sodium chloride. The total amount of protein (TP) and the amounts of albumin (Alb) and globulins (Glo) contained in the plasma before and after treatment are shown in Table 1. The amounts of immunoglobulins (Ig)G, IgA and IgM contained in the globulins are also shown in the table.

TABLE 1

|  | TP (g/dl) | Alb (g/dl) | Glo (g/dl) | IgG (mg/dl) | IgA (mg/dl) | IgM (mg/dl) |
|---|---|---|---|---|---|---|
| BEFORE PROCESSING | 6.4 | 3.8 | 2.6 | 1270 | 216 | 134 |
| AMOUNT OF GLYCINE ADDED  0 | 5.7 | 3.5 | 2.2 | 1180 | 196 | 124 |
| 5 | 4.8 | 3.2 | 1.6 | 680 | 136 | 96 |
| 10 | 4.2 | 3.0 | 1.2 | 380 | 100 | 90 |
| 15 | 3.8 | 2.9 | 0.9 | 240 | 72 | 66 |
| 20 | 3.3 | 2.5 | 0.8 | 90 | 38 | 60 |

The tabulated results show that mixing glycine with sodium chloride greatly enhances the effectiveness of selective precipitative separation of macromolecular protein from plasma.

EXAMPLE 2

Human plasma was treated by using the methodology of Example 1 with a mixture of 30 g/dl (plasma) of sodium chloride and 8 g/dl (plasma) of cystine, 8 g/dl (plasma) of tyrosine or 8 g/dl (plasma) of N-acetyltryptophan. The total amount of protein, the amounts of albumin and globulin, and the ratio (A/G) of albumin to globulin are shown in Table 2. The results of adding glycine in the same concentration as cystine, tyrosine or N-acetyltryptophan are also shown.

TABLE 2

|  |  | TP (g/dl) | Alb (g/dl) | Glo (g/dl) | A/G |
|---|---|---|---|---|---|
| BEFORE PROCESSING |  | 5.8 | 2.5 | 3.3 | 0.76 |
| AMINO ACID ADDED | NONE | 4.0 | 2.1 | 1.9 | 1.11 |
|  | CYSTINE | 3.9 | 2.1 | 1.8 | 1.17 |
|  | TYROCINE | 3.8 | 2.0 | 1.7 | 1.17 |
|  | GLYCINE | 3.0 | 2.0 | 1.0 | 2.00 |
|  | N—ACETYL TRYPTOPHAN | 3.1 | 1.8 | 1.3 | 1.38 |

It will be appreciated from Table 2 that glycine is particularly effective among the amino acids used in the present invention.

As set forth above, the agent for the precipitative separation of proteins from blood plasma according to the present invention enables macromolecular proteins, e.g., immunoglobulins and fibrinogen, to be efficiently removed in large quantity with a high degree of selectivity. When a chloride is used as the alkaline metal salt, even in high concentration, large quantities of such useful proteins as albumin do not precipitate. This is particularly advantageous because it eliminates the need for strict control of concentration. In addition, among the alkaline metal chlorides, use of sodium chloride or potassium chloride is particularly safe since these compounds are present in body fluid.

Further, though the apparatus for separating proteins from blood plasma according to the present invention is simple in construction, the selective precipitative separation of macromolecular protein is possible owing to use of the above-described separating agent. Moreover, by using of a dialyzer for removing the plasma-protein separating agent from the plasma, the effectiveness of plasma purification is enhanced even further since toxic substances having a molecular weight of from several thousand to tens of thousands are removed simultaneously.

It is obvious that if the agent for the precipitative separation of proteins from plasma according to the present invention is used as the solution of the precipitating medium employed in the separating apparatus of FIG. 1 or FIG. 2, the precipitative separating effect can be greatly enhanced.

As many apparently widely different embodiments of the present invention can be made without departing from the spirit and scope thereof, it is to be understood that the invention is not limited to the specific embodiments thereof except as defined in the appended claims.

What we claim is:

1. An apparatus for separation and removal of proteins from blood plasma, comprising:
    a vessel containing an agent for the precipitative separation of proteins from blood plasma, said agent comprising a mixture of an alkaline metal salt and an amino acid in an amount sufficient to promote a fractional precipitating effect of the alkaline metal salt with respect to plasma protein, said amino acid being selected from the group consisting of neutral amino acid, aspartic acid, cystine, N-acetyltryptophan, tyrosine and mixtures thereof;
    means for introducing plasma into said vessel;
    means for separating and removing a precipitate formed inside said vessel by bringing the separating agent and the plasma into contact therein; and
    means for removing at least some of the separating agent constituent from a plasma component which remains following removal of the precipitate.

2. An apparatus for separaton and removal of proteins from blood plasma, comprising:
    a plasma pump for delivering plasma at a predetermined delivery rate, and for returning treated plasma in an amount equivalent to that of the plasma delivered;
    a vessel containing an agent for the precipitative separation of proteins from blood plasma, said agent comprising a mixture of an alkaline metal salt and an amino acid in an amount sufficient to promote a fractional precipitating effect of the alkaline metal salt with respect to plasma protein, said amino acid being selected from the group consisting of neutral amino acid, aspartic acid, cystine, N-acetyltryptophan, tyrosine and mixtures thereof;
    a precipitating medium pump for delivering said agent;
    a mixing unit for mixing the delivered plasma and the delivered agent, whereby a precipitate is formed in said mixing unit;
    a plasma filter for removing the precipitate formed in said mixing unit, thereby resulting in filtered plasma;
    a plasma constituent adjusting unit for removing the agent from the filtered plasma and for producing said treated plasma by adjusting the filtered plasma in terms of water content and electrolyte; and
    a control means for driving and controlling said plasma pump and said precipitating medium pump so that said precipitating medium pump is operatively associated with said plasma pump to deliver said agent at more than the predetermined delivery rate of said plasma pump.

3. The apparatus according to claim 2, wherein said plasma constituent adjusting unit comprises:
    a further plasma pump operatively associated with said plasma pump for operating at a flow rate equal to or less than a delivery flow rate of said plasma pump;
    plasma concentrating means operatively associated with said further plasma pump for removing water from the plasma in an amount equal to or more than the amount of the agent mixed therewith, thereby resulting in concentrated plasma; and
    precipitating medium removing means for removing the agent from the concentrated plasma and for adjusting the electrolyte of the concentrated plasma.

4. The apparatus according to claim 2, wherein said alkaline metal salt is a sodium chloride.

5. The apparatus according to claim 2, wherein said neutral amino acid is a glycine.

6. An apparatus for separation and removal of proteins from blood plasma, comprising:
    a main conduit section having a blood inlet means for receiving blood and a blood outlet means for supplying blood;
    a plasma separator and a plasma-blood mixing unit interposed in fluid communication in said main conduit section between said blood inlet means and said blood outlet means, said plasma separator separating plasma from blood introdcued from the blood inlet;
    a plasma pump for delivering the plasma separated by said plasma separator into a secondary conduit at a predetermined delivery rate, and for delivering treated plasma to said plasma-blood mixing unit in an amount equivalent to that of the plasma delivered into the secondary circuit;
    a vessel containing an agent for the precipitative separation of proteins from blood plasma, said agent comprising a mixture of an alkaline metal salt and an amino acid in an amount sufficient to promote a fractional precipitating effect of the alkaline metal salt with respect to plasma protein, said amino acid being selected from the group consisting of neutral amino acid, aspartic acid, cystine, N-acetyltryptophan, tyrosine and mixtures thereof;
    a precipitating medium pump for delivering said agent;
    a mixing unit for mixing the delivered plasma and the delivered agent, whereby a precipitate is formed in said mixing unit;

a plasma filter for removing the precipitate formed in said mixing unit, thereby resulting in filtered plasma;

a plasma constituent adjusting unit for removing the agent from the filtered plasma and for producing said treated plasma by adjusting the filtered plasma in terms of water content and electrolyte; and a control means for driving and controlling said plasma pump and said precipitating medium pump so that said precipitating medium pump is operatively associated with said plasma pump to deliver said agent at more than the predetermined delivery rate of said plasma pump.

* * * * *